United States Patent [19]

Giuliani et al.

[11] Patent Number: 5,476,384
[45] Date of Patent: Dec. 19, 1995

[54] DENTIFRICE/MEDICATION DISPENSING TOOTHBRUSH

[75] Inventors: David Giuliani, Mercer Island; Roy W. Martin, Redmond, both of Wash.

[73] Assignee: Optiva Corporation, Bellevue, Wash.

[21] Appl. No.: 191,663

[22] Filed: Feb. 4, 1994

Related U.S. Application Data

[62] Division of Ser. No. 999,466, Dec. 29, 1992, Pat. No. 5,309,590, which is a continuation of Ser. No. 626,976, Dec. 13, 1990, abandoned.

[51] Int. Cl.[6] .................................................. A61C 15/00
[52] U.S. Cl. .............................................. 433/216; 15/22.1
[58] Field of Search .............................. 433/86, 119, 216; 601/142, 141, 162; 15/22.1, 22.2, 24, 29

[56] References Cited

U.S. PATENT DOCUMENTS

| 3,375,820 | 4/1968 | Kuris et al. | 601/142 |
|---|---|---|---|
| 3,488,788 | 1/1970 | Robinson | 601/162 |
| 3,547,110 | 12/1970 | Balamuth . | |
| 3,636,947 | 1/1972 | Balamuth | 601/162 |
| 3,809,977 | 5/1974 | Balamuth | 433/86 |
| 3,828,770 | 8/1974 | Kuris et al. | 433/216 |
| 4,012,842 | 3/1977 | Vit | 433/216 |
| 4,787,847 | 11/1988 | Martin et al. | 433/216 |
| 4,961,698 | 10/1990 | Vlock | 433/119 |
| 5,138,733 | 8/1992 | Bock | 433/216 |

Primary Examiner—Cary E. O'Connor
Attorney, Agent, or Firm—Jensen & Puntgam

[57] ABSTRACT

A vibrating toothbrush which includes a brushhead (18) mounted for vibrating movement, a reservoir (30) for containing dentifrice which is located in the handle (14) of the toothbrush, and fluid connecting means (32) connecting the reservoir (30) to the brushhead (18). The brushhead (18) includes either hollow bristles (80) or nozzles (87) in the brushhead (18) to permit egress of the dentifrice from the brushhead (18) in the area of the bristles. The brushhead (18) is driven so as to provide a scrubbing action for the teeth and to provide acoustical energy for acoustical cleansing as well. The action of the brushhead (18) and the load thereon will result in dentifrice being released out of the brushhead (18) or bristles (80) as needed, supporting cavitation and streaming for the acoustical energy, as well as providing the cleansing/therapeutic effect of the dentifrice.

7 Claims, 2 Drawing Sheets

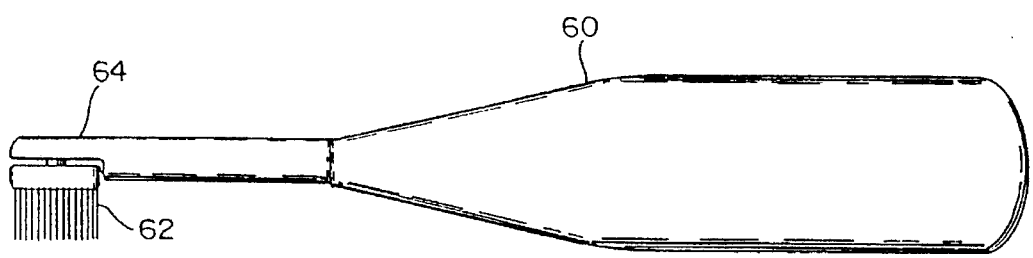
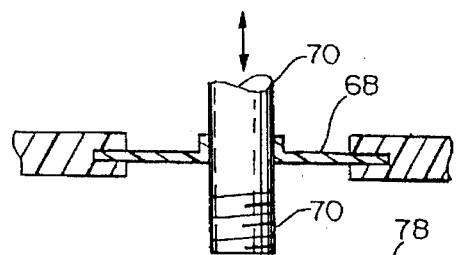
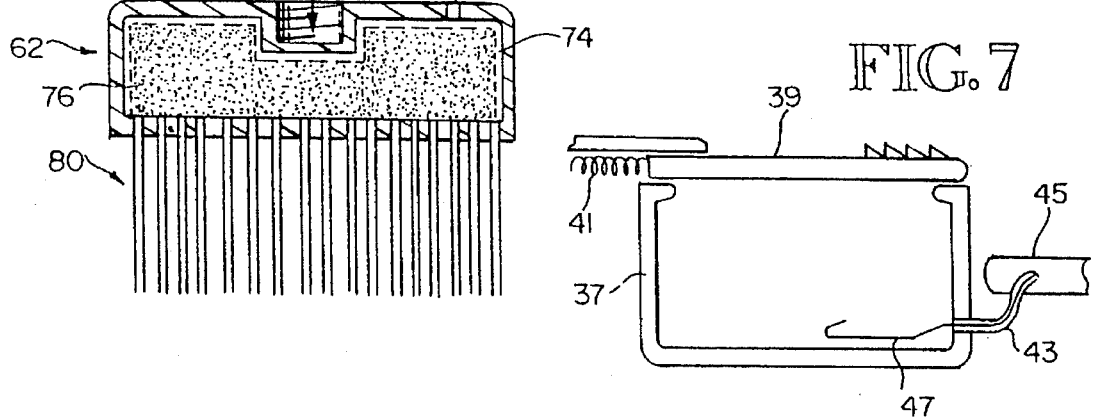
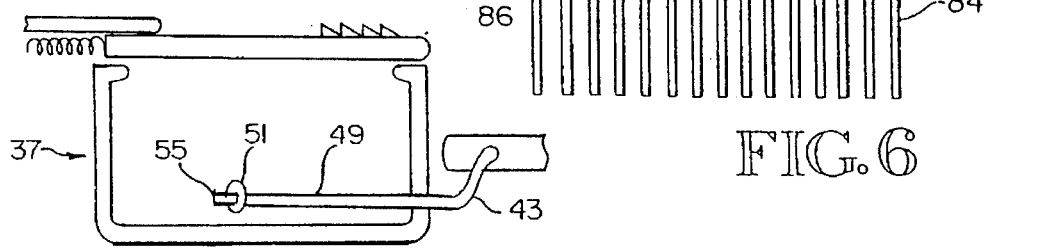

DENTIFRICE/MEDICATION DISPENSING TOOTHBRUSH

This is a divisional of application Ser. No. 999,466, filed on Dec. 29, 1992, now U.S. Pat. No. 5,309,590, which was a continuation of Ser. No. 626,976, filed on Dec. 13, 1990, now abandoned.

TECHNICAL FIELD

This invention relates generally to dental hygiene devices and more specifically concerns a dentifrice/medication dispensing vibrating toothbrush.

BACKGROUND ART

It is well-known that periodontal disease affects a significant portion of the population. It is also well-established that periodontal disease is primarily caused by complex aggregates of microorganisms, primarily bacteria, in the crevice regions between the teeth and the teeth and the gums. These aggregates are commonly referred to as dental plaque.

While brushing with conventional toothbrushes and flossing are currently the standard methods of removing, disrupting and dispersing dental plaque, such techniques have proven to be at best only partially effective, as indicated by the widespread incidence of periodontal disease in the population.

U.S. Pat. No. 4,787,847 is illustrative of a new development in toothbrushes which shows promise in reducing periodontal disease when used regularly. The device utilizes a transducer to produce vibrations in a brushhead, which results in mild cavitation being produced in the gingival (between teeth and gums) fluids in the mouth. This tends to remove the subgingival plaque and to demobilize motile bacteria therein.

However, the device relies on the presence of saliva and toothpaste foam as the medium through which the acoustical energy is conducted and in which cavitation occurs. For many users of the device, this may not be sufficient, especially for the upper teeth. There is no means included in the device for supplying fluid to assure an adequate medium.

In another line of development, medications are known which are capable of inhibiting or killing bacteria responsible for periodontal disease, and the use of such medications has been promoted to the public for such a purpose. Such medications may be used in toothpaste, mouthwash, or solutions applied to the areas of interest. However, such medications are typically expensive when used on a daily basis, have been found to stain teeth in some cases with prolonged use, and in other cases, such as when they are in a mouthwash, are only marginally effective. Applying medication with brushing is convenient for the user and results in the treated area simultaneously undergoing cleaning and the application of medication. However, medication is typically not carefully applied in controlled amounts during brushing. There currently is no convenient way of assuring the application of only therapeutic amounts, so as to prevent waste of the medication, while still being fully effective.

In still another independent line of development in dentistry relating specifically to toothbrushes and toothpaste, it is known to include structure for dispensing a dentifrice in an otherwise conventional toothbrush. In one approach, the toothbrush includes an attachment which dispenses toothpaste in some manner onto the tips of the bristles. Typically, these devices include a reservoir for storing the dentifrice and a means for pumping out the dentifrice from the reservoir onto the tips of the bristles. Examples of this approach include U.S. Pat. No. 4,787,765 and U.S. Pat. No. 4,695,177, both to Kuo. In another approach, dentifrice is dispensed to the base of the toothbrush bristles. U.S. Pat. No. 4,221,492 to Boscardin et al is an example of this approach, as is U.S. Pat. No. 4,655,627 to Bradley, which also discloses a self-sealing reservoir.

U.S. Pat. No. 4,039,261 to Evans shows a still further approach, involving hollow bristles, in which the dentifrice is moved into the bristles at the base thereof and then is moved through the bristles under pressure to the tips. However, the bristles are oversize and do not provide the typical brushing action for the teeth. Also, there is no provision of a cap or similar element to prevent leakage and/or drying of the dentifrice.

The above-described dentifrice-dispensing toothbrushes, however, have several disadvantages. They typically include complicated mechanisms for supplying the dentifrice to the brushes, resulting in inconvenient overall size of the toothbrush, high cost, and reliability problems. Those devices which use pastes have the additional problems of clogging and the formation of hard, cake-like deposits, which prevent reliable flow of the paste when needed. None of these devices supply fluid at a controlled rate which is needed to assure a proper acoustical effect for a vibrating toothbrush, as described above. Further, the lack of fluid control makes such devices unsuitable for use as applicators of therapeutic (medication) agents.

DISCLOSURE OF THE INVENTION

Accordingly, the present invention is a toothbrush having a dentifrice dispensing capability, which includes a toothbrush assembly which includes a toothbrush body, a brushhead in the vicinity of one end of the body having bristles extending therefrom, means for supporting said brushhead for vibrating movement and means for driving said brushhead such that it vibrates. The toothbrush further includes a reservoir for dentifrice, means permitting release of dentifrice from the brushhead and means connecting said reservoir to said release means, wherein said release means is configured and arranged such that in operation of said brushhead dentifrice is discharged from the reservoir through the release means.

BRIEF DESCRIPTION OF THE DRAWINGS

FIG. 4 is a simple schematic diagram of another embodiment of the dentifrice-dispensing toothbrush of the present invention.

FIG. 5 is a cross-sectional diagram of the embodiment of FIG. 4.

FIG. 6 is a cross-sectional diagram showing an alternative embodiment of one portion of the structure of FIG. 5.

FIG. 7 is a cross-sectional diagram showing one embodiment of the dentifrice reservoir portion of the toothbrush of the present invention.

FIG. 8 is a cross-sectional diagram showing a variation of the reservoir embodiment of FIG. 7.

BEST MODE FOR CARRYING OUT THE INVENTION

Figure 1:
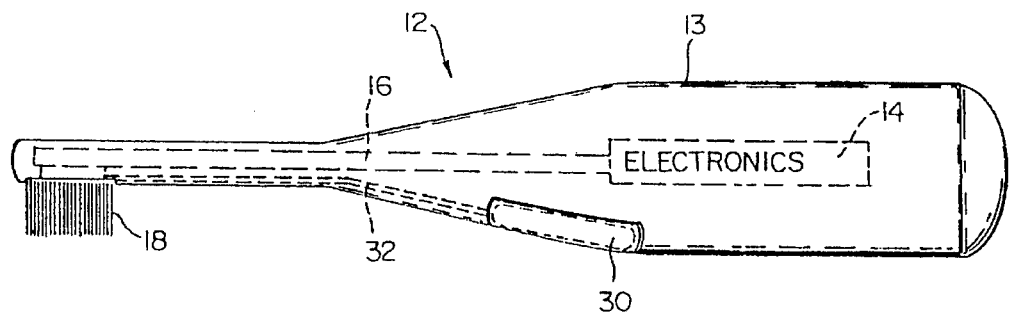
FIG. 1 is a simple schematic diagram of one embodiment of the dentifrice-dispensing toothbrush of the present invention.
Figure 2:
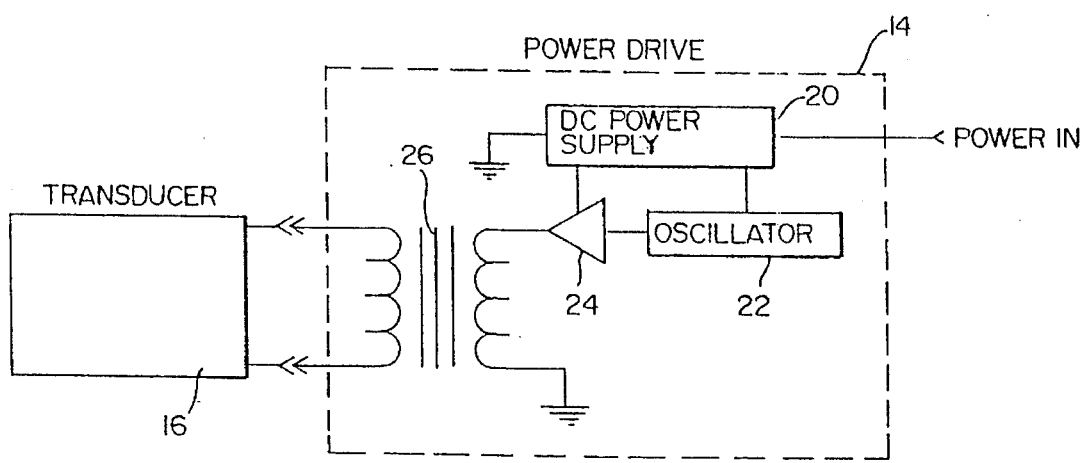
FIG. 2 is a diagram showing the general electrical structure of a vibrating toothbrush.

FIG. 1 shows a simplified schematic diagram of one embodiment of the present invention, while FIG. 2 shows the general electrical structure of an electromechanical vibrating toothbrush. The present invention is thus illustrated and described in the context of a particular toothbrush configuration, i.e. the vibrating toothbrush shown in FIG. 2, but it should be understood that the present invention can be used in other toothbrushes in which the brushhead is vibrated in some manner.

Referring specifically to FIGS. 1 and 2, the vibrating toothbrush includes a body 12 which contains drive electronics 14 located in a handle portion 13 ,and a transducer 16, at the far end of which is positioned a brushhead 18, which extends out from the toothbrush body 12. The brushhead 18 is mounted for vibrating, i.e. up/down or side to side, movement relative to the body 12. The drive electronics 14 comprises basically a DC power supply 20, an oscillator 22, an amplifier 24 and a transformer 26. The output of the transformer acts on a piezoelectric bimorph transducer to produce the movement of the brushhead. The toothbrush structure shown generally in FIG. 2 is explained in more detail in U.S. Pat. No. 4,787,847, which is referred to briefly above and which is incorporated by reference herein.

Figure 3:
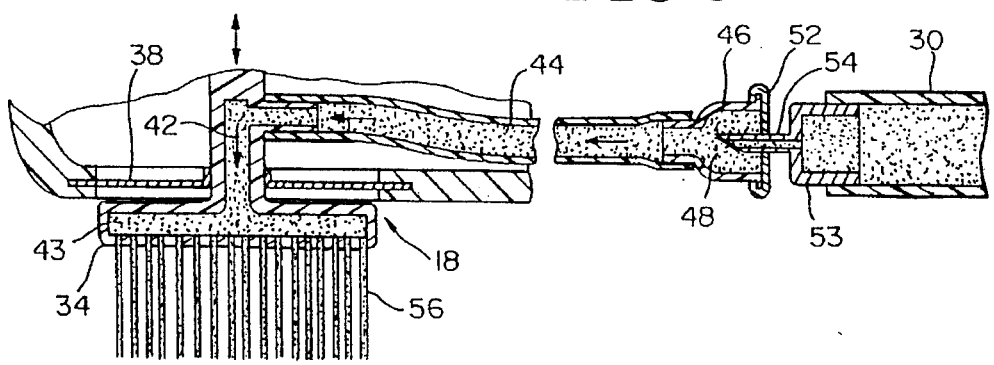
FIG. 3 is a cross-sectional diagram of the embodiment of FIG. 1.

FIG. 1 shows, in the body 12 of the toothbrush, a dentifrice reservoir 30 located in handle portion 13, and a connecting tube element 32 which provides fluid communication between reservoir 30 and brushhead 18. FIG. 3 shows the embodiment of FIG. 1 in more detail. A section of body 12 is shown, as well as the brushhead 18, which is supported within an opening at the end of the body 12 by an isolating membrane 38. Within the brushhead 18 is a channel 42 and a small chamber 43. A tube 44 is connected to channel 42 in the brushhead 18 and extends in body 12 toward handle 13. Tube 44 connects with one end of a bell-shaped casing 46, which has an internal chamber 48. At the other end of casing 46 is a membrane 52. Extending from chamber 48 through membrane 52 and outwardly therefrom is a narrow tube 54 which extends into a cap 53 at the front end of the dentifrice reservoir 30. Such an arrangement permits replacement of the reservoir 30 without introducing air into the other portions of the dentifrice delivery system.

The reservoir 30 is preferably made in the form of a collapsible membrane in order to allow fluid to move from the reservoir without creating a vacuum therein. The collapsible membrane reservoir 30 could, for instance, be a thin wall heat-sealed pouch of vinyl or polyurethane with a tube or rubber o-ring seal. Such a reservoir can be filled, sealed and supplied in a foil wrapped outer pouch to protect any solvents, e.g. alcohol, or oxygen for a gas-releasing dentifrice. The user will remove the membrane reservoir from its outer pouch, attach it to the casing 46 and then prime the system by pushing in on the membrane until dentifrice appears at the bristles. As an alternative to a collapsible membrane, the reservoir 30 could include an air vent.

An alternate embodiment for the reservoir is shown in FIG. 7. In this embodiment, reservoir 37 is positioned within the body of the toothbrush, typically in the handle portion thereof (not shown). The reservoir 37 could also be located within a removable head assembly attached to the body of the toothbrush. The reservoir 37 includes a door 39 which, in one embodiment, could be a thumb-activated sliding door. A spring 41 biases the door 39 to its closed position. The door is not air tight, to provide a vent for the reservoir, but does prevent the dentifrice fluid from leaking out. A tube 43 connects the reservoir 37 to a feed tube 45 which is connected to the vibrating brushhead.

The reservoir 37 could also include a wick element 47, such as a polypropylene felt, which extends between the reservoir 37 and the feed tube 45 in order to prevent air bubbles in the reservoir from moving into the feed tube, thereby maintaining a continuous stream of fluid between the reservoir and the feed tube.

Alternatively, referring to FIG. 8, a flexible tube 49 with a weight 51 could be included in reservoir 37. The flexible tube is connected to or is an extension of connecting tube 43. The weight 51 is positioned near the free open end 55 of flexible tube 49, such that gravity would tend to hold the free open end of tube 49 in any fluid in reservoir 37, regardless of the orientation of the toothbrush and hence the reservoir.

In addition, a sponge member could be placed in the reservoir 37. The sponge comprises a material which is able to store fluid, such as water or a medicine. The sponge will release the fluid as fluid is drawn out of the feed tube.

Referring now again to FIG. 3, a plurality of bristles 56 extend from one surface of the brushhead 34 and are in fluid communication with chamber 43 in the brushhead. A selected number of the bristles are hollow, to permit the correct amount of dentifrice to be dispensed. This arrangement permits the dentifrice to move from the reservoir through the tube 54, the casing 46, the tube 44 and then into the channel 42, the chamber 43, and then through the hollow bristles to the ends thereof, such that in use of the device, the dentifrice is applied to the actual area of interest.

FIGS. 4, 5 and 6 show another embodiment of the present invention and a further variation of a portion of that embodiment. FIG. 4 is a simple schematic view of a vibrating toothbrush which includes a body portion 60 which has a brushhead 62 extending therefrom at one end 64 thereof. The brushhead 62 is mounted and driven for vibratory (i.e. up/down or side to side) action by a drive mechanism such as that described above with respect to the embodiment of FIGS. 1 and 3 and the structure shown in U.S. Pat. No. 4,787,847. Referring to FIG. 4, the brushhead 62 itself contains the dentifrice reservoir. When the dentifrice is depleted, the old brushhead is removed from the driving mechanism and a new one inserted. FIG. 5 shows the brushhead portion of the body 60 of FIG. 4, in which is mounted a supporting membrane 68. The drive plunger 70 is driven by a transducer (not shown) and includes at one end thereof a threaded portion 72 to which may be conveniently removably secured a brushhead 62.

The brushhead 62 includes an interior chamber 74 in which is positioned the fluid reservoir 76 containing the dentifrice. The reservoir 76 comprises a collapsible membrane, so that atmospheric pressure, which is introduced through a pressure relief opening 78 in the brushhead 62, collapses the reservoir 76 as fluid is delivered therefrom. This prevents a vacuum from forming in the reservoir which would impede the flow of dentifrice therefrom. The reservoir 76 is in fluid communication with a plurality of hollow bristles 80 which extend from one side of the brushhead 62. Again, the number of hollow bristles is selected so that the desired amount of dentifrice is dispensed. In operation, the dentifrice is delivered from the reservoir through the hollow bristles to the tips thereof, where it is applied to the area of interest, as the bristles are brought into contact with the teeth and gums.

FIG. 6 shows a variation of the brushhead arrangement of FIGS. 4 and 5, which can also be used in the brushhead of FIG. 1 and 3. Instead of hollow bristles, the bristles 84 are solid, with the area 86 of the brushhead from which the bristles 84 extend including one or more nozzle-like openings 87 therein, which are either in fluid communication with the fluid reservoir 88 in the brushhead (similar to reservoir 76 in FIGS. 4 and 5) or an internal chamber in the brushhead, like chamber 43 in FIG. 3, which contains dentifrice delivered from a remote reservoir.

Dentifrice is supplied to the area of interest by the action of the toothbrush in two ways. One way is through capillary action. Either with the hollow bristle embodiment or with a brush having tufts of solid bristles, as fluid is removed from the vicinity of the brushhead in the use of the device, capillary action draws fluid from the reservoir to replenish what has been used. The more fluid used, the more is replaced. This is true "demand feed" action. Capillary action has been demonstrated over a frequency range of 100–300 Hz. A frequency of 140 Hz for the vibrating toothbrush provides very effective results. It has been found that the supply of fluid when the toothbrush is under a heavy load is nearly twice that when the toothbrush is unloaded. Again, the capillary feed action is due to the use of hollow bristles or by locating solid bristles sufficiently proximate to each other that capillary action occurs.

The other way dentifrice is delivered is through the action of centrifugal force. Centrifugal force produced by the reciprocating vibration of the brushhead acts to force the dentifrice through the hollow bristles or through the nozzles in the brushhead to the vicinity of the tips of the bristles. In both instances, the surface tension properties of the dentifrice and the chambers are such that the dentifrice is retained behind the nozzle or the hollow bristles when the toothbrush is not vibrating, but when the toothbrush is vibrating, sufficient centrifugal force is produced to force the dentifrice out from the nozzles or the bristles. The rate of dispersion of the dentifrice is controlled by the amount of vibration energy of the brushhead, the size of the openings of the nozzles or in the bristles, and the number thereof, as well as the viscosity of the dentifrice.

For a sinusoidal motion of the tip of the bristles of the brushhead, having an amplitude $X(t)=X_o \sin \omega t$, the resulting centrifugal force on an incremental radial section $\Delta r$ will be $F_{66} = A d X_0^2 \omega r \Delta r / G r_o^2$ where A is the area of the fluid column, d is the density of the dentifrice, $X_0$ is the amplitude of the motion of the bristles, $\omega$ is the frequency of oscillation, r is the distance from the center of the motion, $\Delta r$ is the radial thickness of the section, and G equals the gravitational acceleration. The factor G is included so that the force will be expressed in grams. For a column of fluid distributed from $r=0$ to $r=r_0$, the resulting centrifugal force $F_c$ is:

$$F_c = A d X_o^2 \omega^2 / G r_o^2 \int_0^{r_0} r dr = A d X_0^2 \omega^2 / 2G.$$

In a specific example, where $r_0=1.0$ inches, $f=200$ $H_z$d (for water)=16.3 g/inch$^3$, $X_0 = 0.10$ inches, and a tube diameter of 0.10 inches, the resulting force $F_c=2.7$ grams.

This centrifugal force of almost 20 times that of the force of gravity on the same volume of fluid (0.008 inch$^3$) is sufficient to force a fluid through a nozzle or hollow bristle when the brushhead is vibrating, but no drop will move through the nozzle or bristle when the vibration is not present. The centrifugal force is so much stronger than gravity that the fluid delivery performance of the toothbrush is relatively independent of position.

The rate at which fluid is dispensed is controlled by the dimensions of the dispensing mechanism and the choice of fluid. This includes the Size of the exit orifice for the fluid, the fluid pressure and the viscosity of the fluid. The fluid pressure is determined by centrifugal force considerations discussed above. It has been determined by the inventors that rate control under loads of ±15–20% are practical.

While the dentifrice dispensed by the toothbrush of the present invention may be any one of a number of solutions, including a bacterial agent such as an antibiotic like chlorhexidine to control infection, other medications for various treatment and/or preventative purposes may be used, as well as a cleansing or foaming agent, or even water, which will aid the action of the energy of the vibrating toothbrush. The dosage of therapeutic solutions can be carefully controlled and administered simultaneously with the accomplishment of conventional oral hygiene. This can minimize stain buildup. Correct dosages will minimize systemic absorption of the medication. All of these types of solutions and others are included under the general term dentifrice. Preferably, the dentifrice is a fluid.

The medication or dentifrice to be used in the present invention can initially be in the form of a solid pellet, either in a porous bag or in a package form. The dentifrice/medication will be placed in the reservoir along with tap water in which the dentifrice will dissolve. The rate of dissolution can be controlled so that several separate applications may be made with a single pellet or the like.

It should be understood that certain modifications may be made to the present invention to improve its performance. For instance, the reservoir 30 in FIG. 3 may be pressurized in some manner to aid in the flow of dentifrice or a small pump may be attached to the reservoir 30 or at some place along the tube connection to aid in the dispensing of the dentifrice. A small pump could be operated by the power source for the vibrating brushhead. In an example, a pump could be constructed with two one-way valves, surrounding a deformable member which is squeezed by the vibration of the transducer. In another variation, the reservoir 30 could be attachable to a water faucet or the like with a flexible tube connecting the reservoir to the toothbrush. In another variation, the reservoir 30 could be refillable, with water or other dentifrice.

In operation of the toothbrush of the present invention, power is supplied to commence vibration of the brushhead and hence the bristles thereon. This action of the bristles can be used to mechanically "scrub" the teeth to remove food particles and disrupt plaque reachable with the bristles. The user typically will concentrate on the sulcus and interdental regions of the teeth.

The vibrating action of the brushhead also at the same time provides acoustical energy sufficient to support cavitation and streaming throughout the entire mouth area, including areas beyond the reach of the bristle contact. The dentifrice-dispensing feature of the present invention assures effective cavitation and streaming throughout the entire dental area with its active supply of fluid. The acoustical cleaning effect is thus more effective than that which would result by reliance on saliva and toothpaste alone.

The present device thus combines the benefits. of scrubbing bristles with controlled cavitation and streaming, accomplished by the combination of a source of vibration for a brushhead, an appropriate brushhead design and means for supplying fluid at a controlled rate to the brushhead. It should also be noted that the disclosed fluid dispensing mechanism results in the bristles being continuously wet, but not excessively so, which would result in splattering when the device is not in the mouth or in causing the user to remove excess fluid by swallowing, etc., when the device is in actual use. Fluid is supplied basically on demand, to the extent actually needed to maintain effective cavitation and streaming.

A further important advantage of the present invention occurs when the dentifrice is a medicine or chemical agent such as an antibacterial agent, i.e. chlorhexidine. Application of the sonic energy to a medicinal cavitation fluid enhances the effect of the medicinal or chemical agent, thus resulting in a synergistic effect between the acoustical energy of the toothbrush and the medicine or chemical agent. Although it is known generally that acoustic energy can intensify the effect of antibacterial and other chemical agents, the use of acoustic energy delivered by a toothbrush with concurrent delivery of a medicinal agent to provide an enhanced cleansing/medicinal effect for teeth is not believed to be known.

Thus, a new dentifrice-dispensing toothbrush has been disclosed which delivers the dentifrice reliably to an area of interest by virtue of the vibrating action of the toothbrush. This toothbrush permits a careful, accurate targeting of a particular location for application of a dentifrice medication.

The apparatus of the present invention is capable of using the vibration driving source to supply the fluid to the bristles, without the need for a separate pump, although a separate pump can be used. Medication can be automatically applied in precisely controlled amounts during brushing, without the direct intervention of the operator.

Although a preferred embodiment of the invention has been disclosed herein for illustration, it should be understood that various changes, modifications and substitutions may be incorporated in such embodiment without departing from the spirit of the invention as defined by the claims which follow:

We claim:

1. A method of oral hygiene for teeth and the surrounding area, comprising the steps of:

Supplying to the teeth substantially simultaneously in time and space (a) acoustical energy produced by vibrating bristles on a brushhead, wherein the vibrating bristles have an amplitude of movement of at least 0.1 inches, and (b) a fluid, in such a manner as to scrub the teeth and to maintain cavitation in the vicinity of the teeth, disrupting bacteria on the teeth and in areas surrounding the teeth which are not reachable by the bristles.

2. A method of claim 1, wherein the fluid is a medical agent and wherein the acoustic energy interacts with the medicinal agent in such a manner as to enhance the effect of the medicinal agent.

3. A method of claim 2, wherein the medicinal agent is initially is a solid from, but is dissolved prior to application thereof to the teeth.

4. A method of claim 1, wherein the fluid is discharged at least partially by capillary action.

5. A method of claim 1, wherein the fluid is discharged at least partially by centrifugal force.

6. A method of claim 1, wherein the frequency of vibration of the bristles is within the range of 100 to 500 Hz.

7. An oral hygiene apparatus for cleaning teeth and the surrounding area, comprising:

a toothbrush with a brushhead having bristles which extend therefrom;

a reservoir for fluid;

means for vibrating the bristles so as to supply to the teeth substantially simultaneously in time and space (a) acoustical energy produced by vibrating the bristles on the brushhead, the bristles having an amplitude of movement of at least 0.1 inches, and (b) fluid from said reservoir, in such a manner as to scrub the teeth and to maintain cavitation in the vicinity of the teeth, disrupting bacteria on the teeth and in areas surrounding the teeth which are not reachable by the bristles.

* * * * *